United States Patent [19]

Foglio et al.

[11] Patent Number: 5,051,416
[45] Date of Patent: Sep. 24, 1991

[54] ORAL ANTIBACTERIAL METHOD

[75] Inventors: Maurizio Foglio; Giovanni Franceschi; Aurora Sanfilippo, all of Milan, Italy

[73] Assignee: Farmitalia Carlo Erba S.P.A., Milan, Italy

[21] Appl. No.: 331,853

[22] Filed: Apr. 3, 1989

Related U.S. Application Data

[60] Continuation of Ser. No. 906,275, Sep. 10, 1986, abandoned, which is a division of Ser. No. 567,819, Jan. 3, 1984, abandoned.

[30] Foreign Application Priority Data

Jan. 6, 1983 [GB] United Kingdom ................ 8300295

[51] Int. Cl.$^5$ ........................................... H61K 31/43

[52] U.S. Cl. ..................................................... 514/195
[58] Field of Search ............................... 514/192, 195

[56] References Cited

U.S. PATENT DOCUMENTS 4,482,565 11/1984 Fogio et al. ...................... 514/192

Primary Examiner—Jerome D. Goldberg
Attorney, Agent, or Firm—Wegner, Cantor, Mueller & Player

[57] ABSTRACT

A method is provided for treating a warm-blooded animal having a susceptible bacterial infection which comprises administering orally to said animal a non-toxic, antibacterially effective amount of acetoxymethyl ester of (5R,6S)-2(5R,6S)-2-carbamoyloxymethyl-6-[1(R)-hydroxyethyl]-2-penem-3-carboxylic acid.

1 Claim, No Drawings

ORAL ANTIBACTERIAL METHOD

This is a continuation application of U.S. application Ser. No. 906,275, filed Sept. 10, 1986, now abandoned, which is a divisional of Ser. No. 567,819, filed on Jan. 3, 1984, now abandoned.

SUMMARY OF INVENTION

The present invention provides a method of providing high plasma levels of a compound generally within the disclosure of Foglio et al. U.S. Pat. No. 4,482,565. Instead of the acid, salt of esters specifically disclosed by Foglio et al, the present invention provides the oral administration of the acetoxymethyl ester of (5R,6S)-2-carbamoyloxymethyl-6-[1(R)-hydroxyethyl]-2-penem-3-carboxylic acid.

DETAILED DESCRIPTION

Table 1 shows the plasma levels and the area under curve produced when the acetoxymethyl ester of (5R,6S)-2-carbamoyloxymethyl-6-[1(R)-hydroxyethyl]-2-penem-3carboxylic acid was administered orally to mice and rats.

To obtain the results shown in Table 1, the acetoxymethyl ester of (5R,6S)-2-carbamoyloxymethyl-6-[1(R)-hydroxyethyl]-2-penem-3-carboxylic acid was given orally in solution to mice and rats in an amount equivalent to provide 40 mg. of the compound per kg. of body weight after the expected in vivo hydrolysis.

Periodic blood samples were taken from the animals and each assayed for (5R,6S)-2(5R,6S)-2-carbamoyloxymethyl-6-[1(R)hydroxyethyl]-2-penem-3-carboxylic acid content by a standard bio-assay technique.

antibacterial activity either in animals or in humans against both Gram-positive and Gram-negative bacteria the compound of the present invention is useful in the treatment of the infections caused by said microorganisms, such as respiratory tract infections, for example, bronchitis, bronchopneumonia, pleurisy; hepatobiliary and abdominal infections, for example septicemia; urinary tract infections, for example, pyelonephritis, cystitis; obstetrical and gynecological infections, for instance, cervicitis, endometritis; ear, nose and throat infections, for instance, otitis, sinusitis, parotitis. The toxicity of the compounds of the invention is quite low and therefore they can be safely used in therapy.

The compound of the invention is useful in the treatment of bacterial infections in mammals, including man. It is administered orally and may be in capsule form, or as tablets, powders, liquid solution, suspensions, elixirs, or the like. The compound may be used alone or in combination with other active ingredients. It may be used in compositions including one or more pharmaceutically acceptable carriers or diluents as well as other ingredients such as stabilizers, binders, antioxidants, preservatives, lubricating agents, suspending agents, viscosity agents and/or flavorings.

Acceptable carriers and diluents are, for example, water, gelatin, lactose, starches, magnesium stearate, talc, vegetable oils and cellulose.

Daily doses in the range of about 1 to about 100 mg per kg of body weight may be used, in various animal species, the exact dose depending on the age, weight and condition of the subject to be treated and on the frequency of administration. The compound is administered, for example, to adult humans, in an amount ranging from about 100 mg to about 300 mg pro dose, prefer-

| Species | Ester of PCE 22101 | Mean plasma concentration (ug/ml) of PCE 22101 minutes after administration | | | | | | | Area under curve ug min./ml | Peak plasma concentration |
|---|---|---|---|---|---|---|---|---|---|---|
| | | 2 | 4 | 5 | 6 | 10 | 20 | 30 | 45 | | |
| Mouse | Acetoxymethyl | 13.5 | 21 | — | 19.5 | 11.2 | 3.5 | 1.12 | 0.78 | 253.8 | 21 |

| Species | Ester of PCE 22101 | Mean plasma concentration (ug/ml) of PCE 22101 minutes after administration | | | | | | | Area under curve ug min./ml | Peak plasma concentration |
|---|---|---|---|---|---|---|---|---|---|---|
| | | 5 | 10 | 15 | 20 | 30 | 45 | 60 | 75 | | |
| Rat | Acetoxymethyl | 5.8 | 10 | — | 4.1 | 6.5 | 2.7 | 1.8 | 1.2 | 288.36 | 10 |

The data in Table 1 demonstrate that the ester of PCE 22101 is orally adsorbed and then hydrolised in blood to give the active drug. Penem carboxylic acids and their sodium salts described in the above cited British Patent Specification are not adsorbed as such in the stomach and intestinal tract.

The therapeutic efficacy in mice, tested after oral administration, confirmed the bio-availability of the antibiotic by oral route, with $ED_{50}$ comparable to (5R,6S)-2(5R,6S)-2-carbamoyloxymethyl-6-[1(R)-hydroxyethyl]-2-penem-3-carboxylic acid given subcutaneously as reported in Table 2.

TABLE 2

| Compound | Administration Route | Infection i.p. | $ED_{50}$ mg/kg |
|---|---|---|---|
| Acetoxymethyl ester compound* | per os | per os | 3.2 |
| Compound* | s.c. | Staf. aureus Smith | 1 |

* = (5R,6S)-2(5R,6S)-2-carbamoyloxymethyl-6-[1(R)-hydroxyethyl]-2-penem-3-carboxylic acid The acetoxymethyl ester of (5R,6S)-2-carbamoyloxymethyl-6-[1(R)-hydroxyethyl]-2-penem-3-carboxylic acid is particularly valuable owing to its efficacy for various bacterial. More specifically, owing to the high ably about 200 mg pro dose, 1–4 times a day. It is also useful as nutritional supplements in animal feeds.

The following examples illustrate the invention.

EXAMPLE

Acetoxymethyl-(5R,6S)-2-carbamoyloxymethyl-6-[1(R)-hydroxyethyl]-2-penem-3-carboxylate.

1.3 g of sodium (5R,6S)-2-carbamoyloxymethyl-6-[1(R)-hydroxy-ethyl]-2-penem-3-carboxylate, produced in accordance with Foglio et al. U.S. Pat. No. 4,482,565, were dissolved in 30 ml of anhydrous dimethylformamide and treated with 0.65 g of acetoxymethylbromide at room temperature for 3 hours.

The reaction mixture was then diluted with ethyl acetate, washed with water, dried over sodium sulphate and evaporated.

The obtained crude compound was crystallized from chloroform-cyclohexane and then from hot chloroform;

m.p. 127° C. (from CHCl₃); [a]²⁰ = +137° (1% in acetone). I>R>(KBr): $_{max}$ (EtOH 95%) 327 nm (7800). P,M,E, (200 MHz, acetone d₆), (ppm): 1.26 (d, J=6.0 Hz, 3H, CH₃CH). 3.78 (s, 1H, OH). 3.80 (dd, J=1.7 and 6.4 Hz, 1H, H-6). 4.14 (m, 1H, CH₃CH). 5.08, 5.34 (two d, J=16.0 Hz, 2H, CH₂OCONH₂). 5.69 (d, J-1.7 Hz, 1H, H-5). 5.80 5.86 (two d, J=5.8 Hz, 2H, COOCH₂OCO). 6.10 (bs, 2H, NH₂.

What is claimed is:

1. A method of treating a warm-blooded animal having a susceptible bacterial infection which comprises administering orally to said animal a non-toxic, antibacterially effective amount of the acetoxymethyl ester of (5R,6S)-2(5R,6S)-2-carbamoyloxymethyl-6-[1(R)-hydroxyethyl]-2-penem-3-carboxylic acid.

* * * * *